(12) United States Patent
Borden et al.

(10) Patent No.: US 8,617,892 B2
(45) Date of Patent: Dec. 31, 2013

(54) MICROBUBBLE DEVICES, METHODS AND SYSTEMS

(75) Inventors: Mark A. Borden, Boulder, CO (US); Eric G. Lima, Patterson, NY (US); Clark T. Hung, Ardsley, NY (US); Shashank Ramesh Sirsi, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/393,273

(22) PCT Filed: Aug. 31, 2010

(86) PCT No.: PCT/US2010/047263
§ 371 (c)(1),
(2), (4) Date: Apr. 30, 2012

(87) PCT Pub. No.: WO2011/028690
PCT Pub. Date: Mar. 10, 2011

(65) Prior Publication Data
US 2012/0214238 A1     Aug. 23, 2012

Related U.S. Application Data

(60) Provisional application No. 61/304,782, filed on Feb. 15, 2010, provisional application No. 61/239,000, filed on Sep. 1, 2009.

(51) Int. Cl.
*C12N 5/00*     (2006.01)

(52) U.S. Cl.
USPC ............................. 435/397; 435/395; 435/325

(58) Field of Classification Search
None
See application file for complete search history.

(56) References Cited

U.S. PATENT DOCUMENTS

| | | | |
|---|---|---|---|
| 6,210,611 | B1 | 4/2001 | Needham et al. |
| 6,245,318 | B1 | 6/2001 | Klibanov et al. |
| 6,703,047 | B2 | 3/2004 | Sawhney et al. |
| 2005/0260189 | A1 | 11/2005 | Klibanov et al. |
| 2009/0123435 | A1 | 5/2009 | Ratcliffe et al. |
| 2010/0166668 | A1 | 7/2010 | Wei et al. |

OTHER PUBLICATIONS

Demarteau et al., Biochemic. Biophysic. Res. Comm., 310:580-588 (2003).*
Nair et al., Engineering in Medicine and Biology Workshop, IEEE Dallas, 31-34 (2007).*
Terraciano et al., Stem Cells 25:2730-2738 (2007).*
Achilli, PhD Thesis: Physically Crosslinked Chitosan Based Hydrogels for Biomedical Applications, Abstract (2008).*
Nair, PhD Thesis: Novel Preparation of Polymeric Scaffolds for Tissue Engineering Using Phase Separation With Protein Microbubble Incorporation (2006).*

(Continued)

*Primary Examiner* — Blaine Lankford
*Assistant Examiner* — Thomas J Visone
(74) *Attorney, Agent, or Firm* — Miles & Stockbridge, P.C.; Mark A. Catan

(57) ABSTRACT

A hydrogel tissue engineering scaffold having microbubbles dispersed therein is disclosed. Also, a system for cell culturing including a controller and actuator to apply dynamic deformational loading to a hydrogel is disclosed. Also disclosed are methods for producing hydrogels with microbubbles and for culturing cells using hydrogels with microbubbles.

14 Claims, 15 Drawing Sheets

(56) References Cited

OTHER PUBLICATIONS

Cavalieri et al., "Stable Polymeric Microballoons as Multifunctional Device for Biomedical Uses: Synthesis and Characterization," *Langmuir*, 2005, 21(19): pp. 8758-8764.

Chappell et al., "Targeted Delivery of Nanoparticles Bearing Fibroblast Growth Factor-2 by Ultrasonic Microbubble Destruction for Therapeutic Arteriogenesis," *Small*, Oct. 2008, 4(10): pp. 1769-1777.

Nair et al., "Novel Polymeric Scaffolds Using Protein Microbubbles as Porogen and Growth Factor Carriers," *Tissue engineering: Part C—Methods*, Feb. 2010, 16(1): pp. 23-32.

* cited by examiner

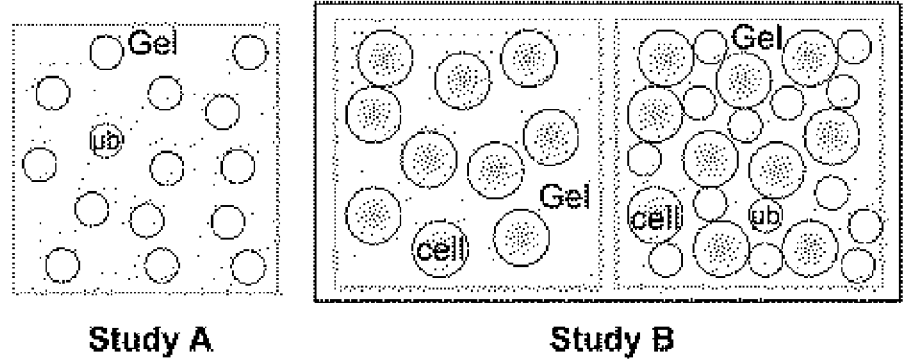
Fig. 5 Schematic of design. µb: microbubble
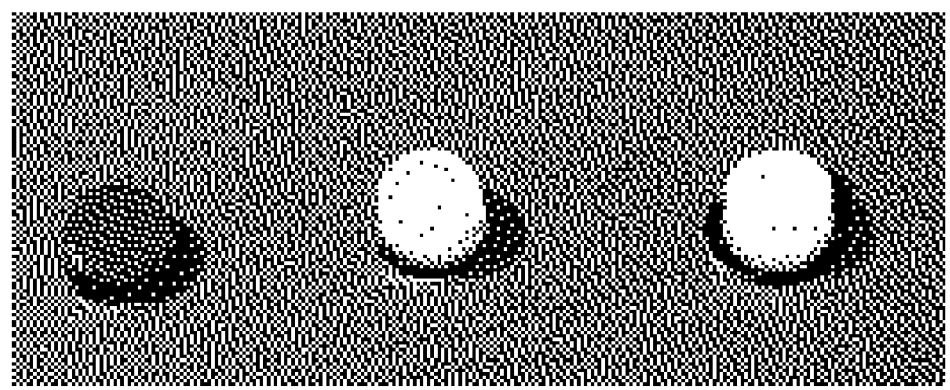
Fig. 6 Freshly cast acellular agarose discs with varying concentrations of microbubbles. From left to right, ctrl (no bubbles), 1.5 x10$^8$, and 3x10$^8$ bubbles/mL.

Cross-sectional image showing bubbles (black dots) on Day 0 of 7-day culture period (bar=20 μm).

Cross-sectional image showing loss of bubbles (black dots) over 7-day culture period (bar=20 μm).

Normalized partition coefficient (κ) of 70 kDa dextran (day 28 normalized to day 0 values), *p<0.01 against all other groups.

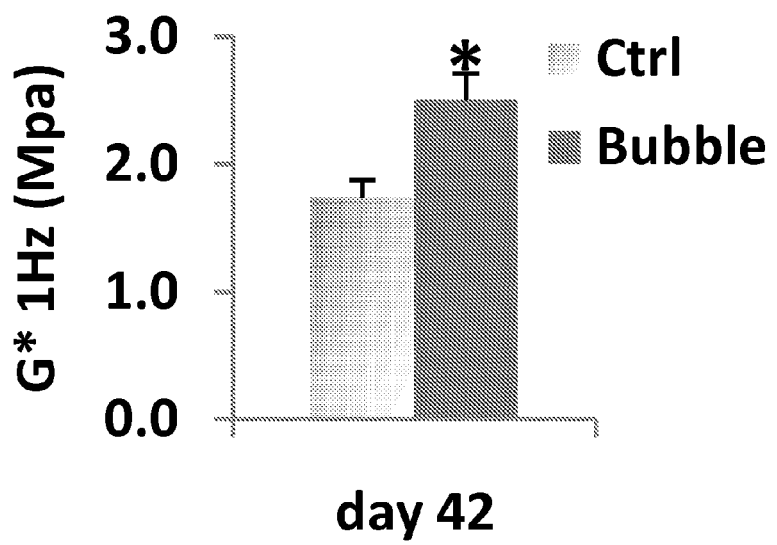
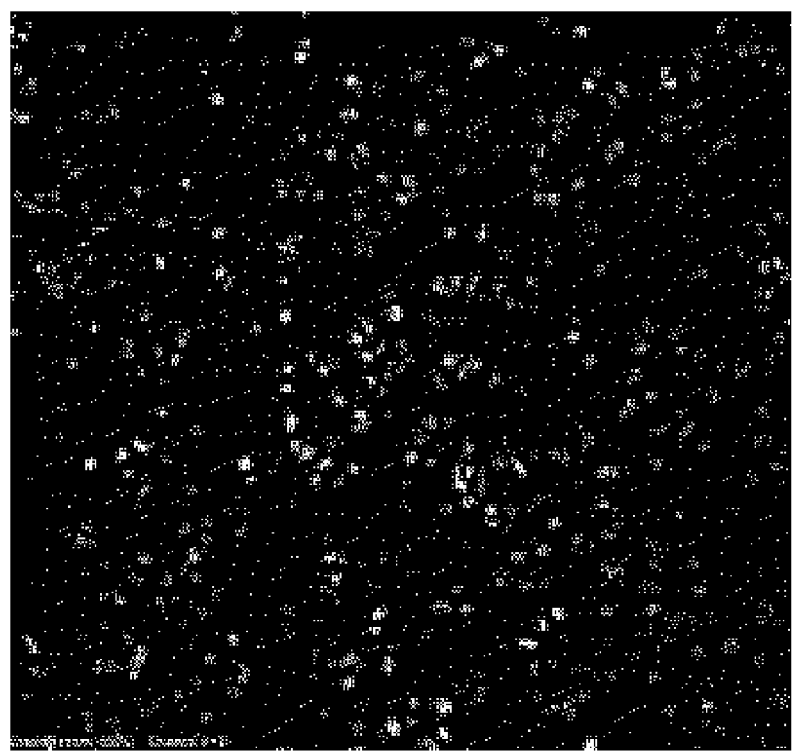
Fig. 8
Dynamic Modulus on day 42 chondrocyte-seeded discs w/wo bubbles, *p<0.01.Live/Dead image on day 42 (bar=100 μm)

A) Schematic of solute diffusion path in hydrogel (i) with gas microbubbles (pb) (ii) and fluid-filled pores after pb dissolution (iii). B) Microbubbles suspended in hydrogel (bar: 10 pm). C) Microbubble infused hydrogel construct pre/post partial microbubble dissolution was triggered (becoming less opaque).

Engineered knee cap (patella) construct showing proteoglycan-rich matrix (red safranin-O stain) limited to gel periphery indicating diffusion limitations. *interface between gel-bony substrate.

A) Nutrient limitations lead to lower tissue mechanical properties for chondrocyte-seeded agarose constructs due to development of axial inhomogeneity (2 mm thick). More uniform properties, and overall higher modulus, are achieved in a 1 mm thick construct . Serum-free media.

Schematic of hydrogel conditions to be studied, cellular constructs ± microbubbles (pb).

Chondrocyte-seeded agarose hydrogel constructs (2 mm thick) develop axial inhomogeneous mechanical properties with culture time. FS: free swelling and DL: dynamic loading (10% deformation, 1 Hz, 3 hours/daily, 20% FBS media).

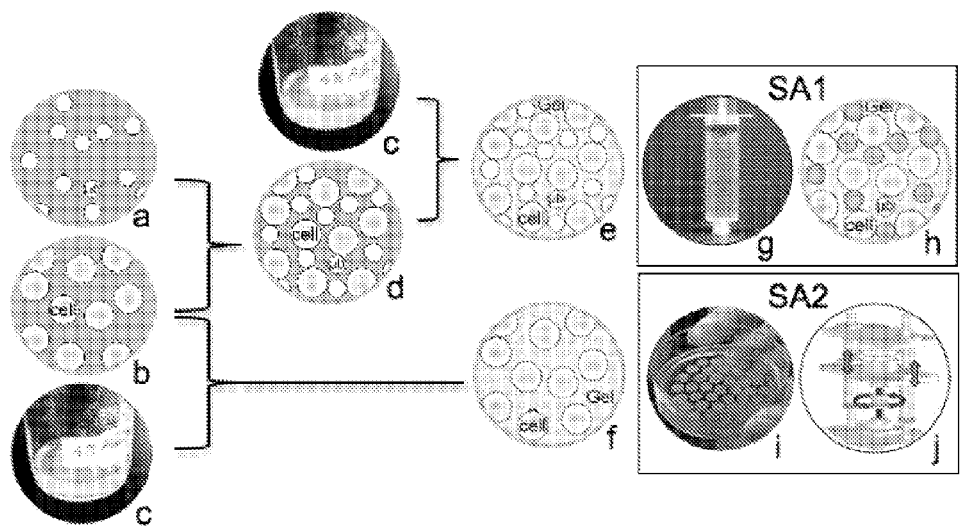

Fig. 14

A solution of microbubbles (a) and solution of chondrocytes (b) will be combined (d) and mixed with an equal volume of 4% agarose hydrogel (c) to fabricate chondrocyte-seeded, microbubble infused agarose constructs (e). Control chondrocyte-seeded agarose constructs (f) will be fabricated by combining equal volumes of (b) and (c). Microbubble dissolution in constructs will be triggered using hydrostatic pressure (g), creating fluid-filled macro-pores (h), and constructs cultured under free-swelling (i) or dynamic deformational loading (j) conditions for up to 56 days.

Microbubbles in solution (A), and in hydrogel (A inset). B) Acellular hydrogel constructs with increasing microbubble volume fraction. C) Properties of microbubble infused acellular hydrogels. *p<0.05 vs. control (0%).

Gas-filled microbubble (noted by red ellipse) in hydrogel constructs subjected to hydrostatic pressure, become fluid-filled.

A) Dynamic modulus (G*), B) vital staining and C) safranin-O staining for GAG of chondrocyte-seeded agarose constructs infused with microbubbles and cultured for 28 days. Control: 2% agarose construct without bubbles.

MICROBUBBLE DEVICES, METHODS AND SYSTEMS

CROSS-REFERENCE TO RELATED APPLICATIONS

The present application is a U.S. national stage of International Application No. PCT/US10/47263, filed Aug. 31, 2010, which claims the benefit of U.S. Provisional Application No. 61/239,000, entitled "Using Gas-Filled Microbubbles to Alter the Physical Properties of Hydrogels for Tissue Engineering," filed on Sep. 1, 2009, and U.S. Provisional Application No. 61/304,782, entitled "Gas-Filled Microbubbles Devices Methods and Systems," filed on Feb. 15, 2010, all of which are incorporated by reference herein in their entireties.

STATEMENT REGARDING FEDERALLY SPONSORED RESEARCH

This invention was made with government support under AR046568 awarded by the National Institutes of Health (NIH). The government has certain rights in the invention.

SUMMARY

Damage to articular cartilage is a common condition affecting the joints of millions of people. This is a major problem considering the poor regenerative capacity of adult articular cartilage and the disability and pain that accompanies these injuries. An estimated 27 million Americans age 25 and older have osteoarthritis (OA). The total direct cost of OA is estimated at $28.6 billion dollars a year in related medical costs. More than 680,000 arthroplastic procedures are performed each year in the U.S.

Tissue engineering strategies promise improvements in health care for conditions such as damaged cartilage. Effective treatment of cartilage injuries using tissue engineering strategies may prevent the development of OA and may reduce the need for a total joint replacement. While tissue engineering strategies hold promise for new treatment options, challenges remain.

For example, the ability to supply nutrients to cells is a useful feature of engineered tissues but an overly porous scaffold can result in cell product loss to the culture medium rather than its retention. An insufficiently porous scaffold or medium can lead to nutrient deficiencies for cells at the construct core region (e.g., regions remote from perfused surfaces). Striking a balance between these factors is challenging as construct dimensions increase or as cells deposit matrix with time in culture. A preferred scaffold has a global architecture that uniformly distributes nutrients throughout while maintaining an optimal local pore-structure around cells.

Hydrogels may provide three-dimensional scaffolds for cartilage basic science and tissue engineering applications due to their inherent similarities to native cartilage, including high water content, ability to maintain the chondrocyte phenotype as well as ease of uniform cell seeding. Hydrogel crosslinking density defines the local pore size around encapsulated cells responsible for entrapment of cell-synthesized molecules that form extracellular matrix (ECM) tissue. If porosity is too high, cell products are released into the bathing culture media, whereas if the porosity is too low, cells become nutrient limited.

Embodiments of the present invention were conceived in light of the above mentioned tissue engineering challenges, among other things.

In an embodiment, microbubbles are used to modify the properties of a clinically-relevant hydrogel scaffold for applications such as cartilage tissue engineering. Microbubble-dispersed hydrogel constructs may be characterized in terms of their physical properties (e.g., mechanical properties, diffusivity) with culture time; as well as their biocompatibility in culture.

An embodiment includes the application of microbubble technology as a means of fabricating cell seeded hydrogel scaffold constructs that retain an optimal polymer crosslinking density for extracellular matrix production/retention while providing a uniform macro-porosity that increases the effective diffusivity of soluble factors into cell-seeded scaffolds may provide benefits as discussed herein. Strategies may include triggering the dissolution of microbubbles, permitting them to become fluid-filled, and acting as macropores thereby reducing path length an increasing nutrient transport and signaling.

In another embodiment, a method of altering the physical properties of a clinically-relevant hydrogel scaffold includes incorporating gas-filled microbubbles into the hydrogel scaffold, whereby the physical properties are altered such that the effective diffusivity of nutrients is increased. An exemplary method further includes mixing gas-filled microbubbles with molten agarose solutions at concentrations ranging from $1\times10^8$ to $1\times10^9$ microbubbles per milliliter (μb/mL); and allowing the solution to cool so that the gel solidifies with the bubbles contained inside. This method allows the size and concentration of the bubbles to be carefully controlled and further allows for a very uniform distribution of bubbles to be maintained. Additionally, this method yields no cell toxicity resulting from the formulation process.

BRIEF DESCRIPTION OF THE DRAWINGS

FIG. 5 is a schematic depiction of microbubble design and characterization in two studies.

FIG. 6 is a series of acellular agarose discs with varying concentrations of microbubbles.

FIG. 8 is a graph of a dynamic modulus in constructs of varying microbubble concentration.

FIG. 14 illustrates a procedure according to embodiments of the disclosed subject matter.

DETAILED DESCRIPTION

Figure 1:
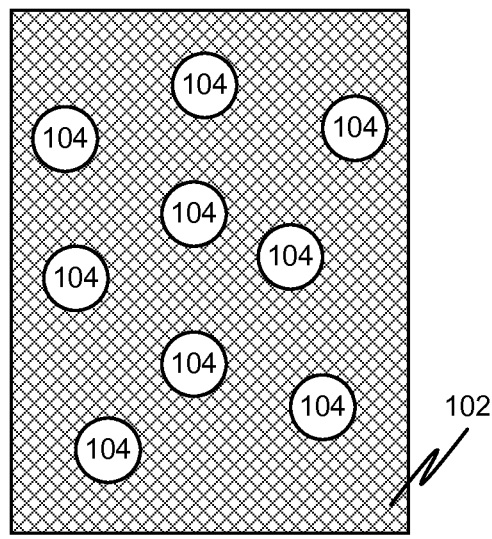
FIG. 1 is a diagram of a hydrogel scaffold with dispersed microbubbles in accordance with the present disclosure.

FIG. 1 is a diagram of a hydrogel scaffold 102 with dispersed microbubbles 104 in accordance with the present disclosure. The hydrogel 102 may be a tissue engineering scaffold. A tissue engineering scaffold may provide nutrient exchange to cells embedded therein. This is particularly advantageous in scaffolds of relatively greater thickness. The tissue engineering scaffolds further provides for cellular division and expansion in a three-dimensional matrix wherein the third dimension (i.e., thickness) is substantially proportionate to the other dimensions. Additionally, the tissue engineering scaffold may be used to achieve native tissue properties in relatively small samples.

Microbubbles may be formulated by emulsifying a lipid formulation with a hydrophobic gas, sulfur hexafluoride (SF6) or perfluorobutane (PFB). The lipid formulation consists of lipid molar ratios of 90% 1,2-distearoyl-sn-glycero-3-phosphocholine (DSPC) and 10% Polyethylene Glycol (40) Stearate (PEG-40). The microbubbles may be formulated with other emulsifying agents as well, including but not limited to, 1,2-dimyristoyl-sn-glycero-3-phosphoethanolamine-N-[methoxy(polyethylene glycol)-2000](DSPE-PEG2K), 1,2-dimyristoyl-sn-glycero-3-phosphoethanolamine-N-[methoxy(polyethylene glycol)-5000] (DSPE-PEG5K), and other DSPE-PEG variants.

Figure 2:
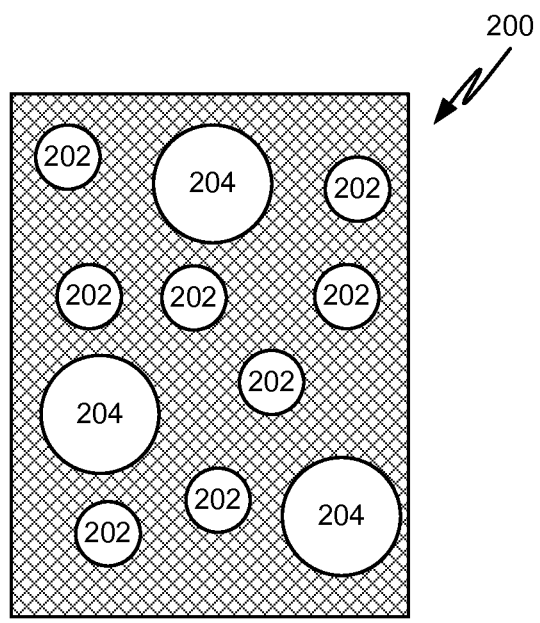
FIG. 2 is a diagram of a hydrogel scaffold with dispersed microbubbles and cells in accordance with the present disclosure.

FIG. 2 is a diagram of a hydrogel tissue engineering scaffold 200 having dispersed microbubbles 202 and cells 204. The cells 204 may be chondrocyte cells, or any other type of cell suitable for tissue engineering.

Figure 3:
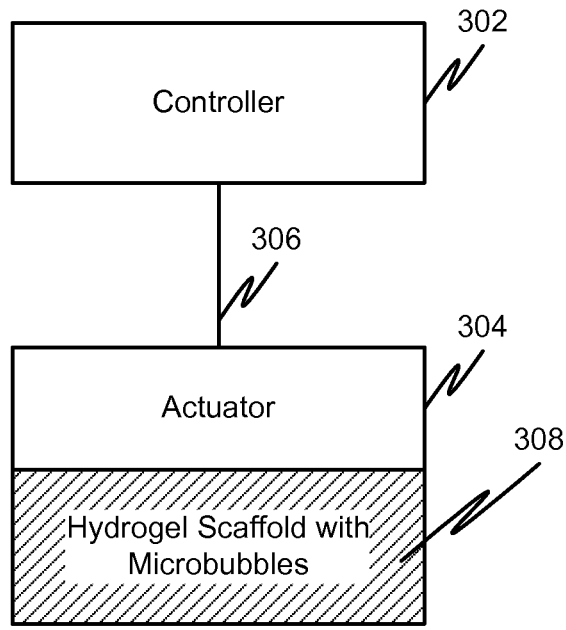
FIG. 3 is an automatic tissue culture system in accordance with the present disclosure.

FIG. 3 is a system for dynamic deformational loading of a hydrogel tissue engineering scaffold adapted to culture cells. In particular, a system 300 includes a processor 302 and an actuator 304 coupled to the processor 302 via a link 306. The actuator 304 is disposed adjacent to a hydrogel scaffold 308.

In operation, the processor 302 is programmed to activate the actuator 304 according to a predetermined timing. For example, the processor 302 may apply dynamic deformational loading at one or more predetermined times during a cell culture cycle. The system may continue to further culture the cells after the one or more applications of dynamic deformational loading. The dynamic deformational loading may have an amplitude that destroys some or all of the microbubbles and releases gas from microbubbles within the hydrogel and allows liquids (e.g., nutrients) to fill the spaces previously occupied by the microbubbles. The loading may have an amplitude that places a load on the hydrogel, but does not destroy all, or a significant portion, of the microbubbles.

Figure 4:
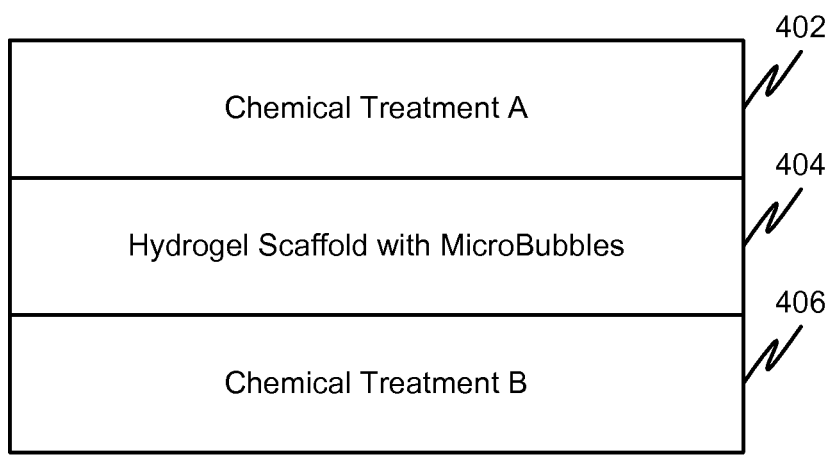
FIG. 4 is a diagram of a hydrogel scaffold with two chemical treatments in accordance with the present disclosure.

FIG. 4 is a cell culture system 400 in which a first chemical treatment 402 is applied to a top surface of a hydrogel scaffold 404. A second chemical treatment 406 is applied to a bottom surface of the hydrogel scaffold 404. The first chemical treatment 402 and the second chemical treatment 406 can be the same or different. The hydrogel scaffold 404 may have gas-filled microbubbles incorporated such that the hydrogel scaffold 404 floats above the second chemical treatment 406 and below the first chemical treatment 402.

The present inventors conducted two studies, Study A and Study B, to characterize microbubble-dispersed hydrogel constructs in terms of their (1) physical properties (e.g., mechanical properties, diffusivity) with culture time; as well as their (2) biocompatibility in culture. See, for example, Study A and Study B, shown in FIG. 5.

As part of Study A, microbubbles were created through sonication of distearoyl-phosphatidylcholine (DSPC) lipid with perfluorobutane (PFB) gas. The bubbles in the resulting mixture were counted and sized (~0.5-10 µm) and combined with agarose to create acellular discs of three concentrations. FIG. 6 shows freshly cast acellular agarose with microbubble concentrations of 0, 1.5, and $3 \times 10^8$ bubbles/mL. The discs were maintained in PBS at 37° in an incubator for 28 days and examined for changes in mechanical properties, changes in bubble density, and changes in diffusivity. Microscope testing with digital image correlation was used to evaluate changes in mechanical properties. Changes in diffusivity were tested for using fluorescently tagged 70 kDa dextran.

Figure 7A:
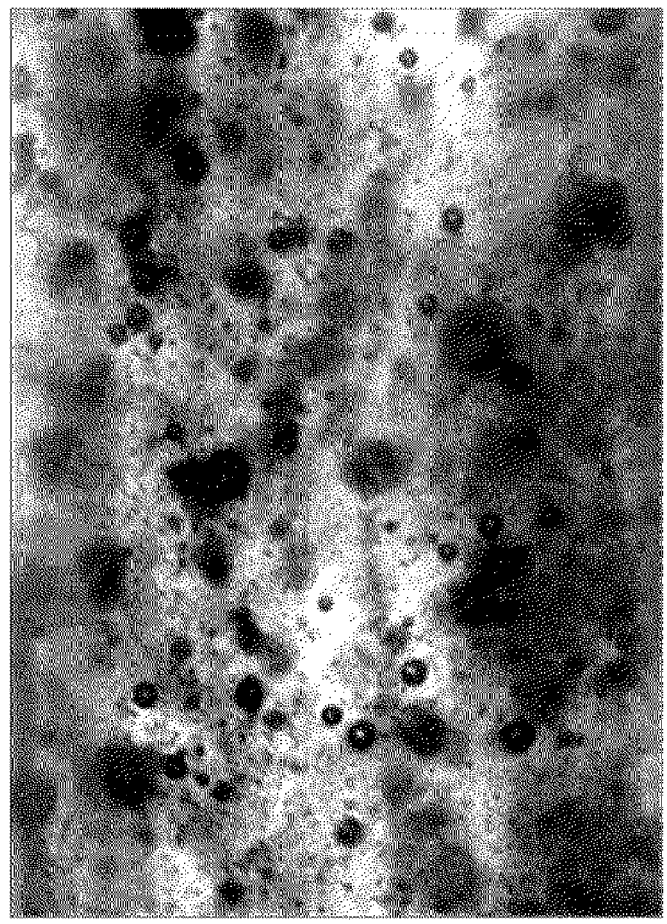
FIG. 7A is a cross-sectional image showing microbubble concentration in a construct on day 0 of a cell culture cycle.
Figure 7B:
FIG. 7B is a cross-sectional image showing microbubble concentration in a construct on day 7 of a cell culture cycle.
Figure 7C:
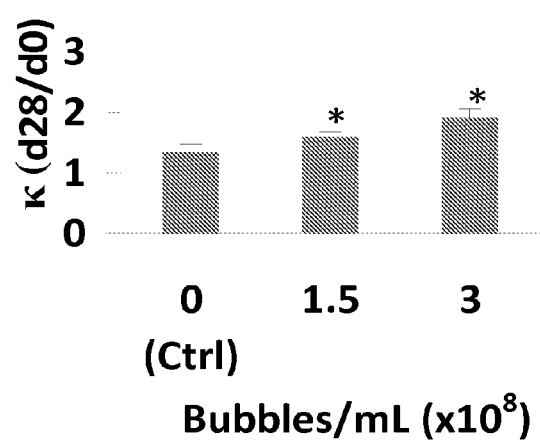
FIG. 7C is a graph of effective diffusivity in constructs of varying microbubble concentration.

By day 7, bubbles were no longer visible under the microscope, whereas they were highly visible on initial casting. See, for example, FIGS. 8A and 8B. Higher concentrations of bubbles created higher opacity in constructs, as shown in FIG. 7, and decreased Young's modulus. For example the control construct exhibited a Young's modulus of 11.31±2.2 kPa, the construct having a microbubble (µb) concentration of 1.5× $10^8$ bubbles/mL showed a Young's modulus of 9.3±1.1 kPa, and the construct having a µb concentration of $3.0 \times 10^8$ bubbles/mL showed a Young's modulus of 7.75±1.4 kPa. Local mechanical measurements performed using digital image correlation and a custom microscopy-based material testing device indicated a uniform strain field across the constructs with and without microbubbles throughout the study (not shown). By day 28, the effective diffusivity of 70 kDa dextran increased significantly over day 0 values and over day 28 controls. See, for example, FIG. 8.

Study B included an initial biocompatibility study; microbubbles were created by vigorous shaking of DSPC lipid in the presence of PFB gas using a dental amalgamator. The resulting bubble mixture was combined with primary chondrocytes ($30 \times 10^6$ cells/mL) isolated from fresh bovine wrist joints and suspended in molten agarose (Type VII, Sigma). Cylindrical discs (Ø4×2.3 mm) were cast and cultured for 42 days in chemically-defined Dulbecco's Modified Eagle Medium (DMEM) according to an optimized protocol. Constructs were examined for changes in mechanical and biochemical properties and cell viability. Changes in mechanical properties were evaluated based on, for example, Young's modulus and dynamic modulus at 1 Hz using a custom material testing device. Changes in biochemical properties were evaluated based on, for example, glycosaminoglycans (GAG) using the 1,9-dimethylmethylene blue (DMMB) assay Cell viability was evaluated using live/dead staining.

Cells in the bubble group remained viable throughout the 42-day study and developed, for example, a higher dynamic modulus than the control (bubble free) group, as shown in FIG. 4. There were no apparent differences in Young's modulus, GAG (e.g., bubble=10.8±1.2% ww, Control=9.5±1.4% ww) or collagen content (e.g., bubble=2.1±0.5% ww, Control=2.0±0.4% ww).

As can be readily seen from Study A and Study B, for example, microbubble incorporation may result in changes to hydrogel scaffold physical properties. The candidate hydrogel of study was clinically-relevant agarose, but other hydrogel materials (e.g., alginate, PEG) may be used. The ability to combine microbubbles and cells into the molten hydrogel before gel polymerization permits hydrogel constructs to be fabricated without modifying standard protocols. Moreover, this ability retains the advantage of uniform cell seeding typically associated with hydrogel scaffolds. This is more challenging to achieve for pre-fabricated fibrous or porous scaffolds that require a secondary cell seeding step.

Providing adequate nutrient access to cells becomes increasingly difficult with engineered constructs of increasing dimensions. Culturing anatomically-shaped constructs, for example, pose a significant challenge due to nutrient limitations at the heart of these large constructs. The diffusivity measurement presented here suggests that incorporation of dispersed microbubbles in agarose increases access of nutrients. See, for example, Study A. These results may help explain the enhanced tissue properties observed in the cellular study. See, for example, Study B. Future studies will be performed to identify the specific mechanisms mediating the enhanced tissue development associated with microbubble incorporation into the hydrogel scaffolds.

Under culture conditions, the encapsulated bubbles dissolved within a week. The transitory nature of the bubbles may serve to leave behind pores that alter the structure and properties of the scaffold. These pores, in turn, may fill with the surrounding nutrient medium. Bubble properties may be modulated to extend the stability of the bubbles in culture as well as incorporation of growth factors to their surfaces. In addition to their other uses, microbubbles may have potential for applications in regenerative medicine strategies for cartilage repair. Other potential applications include, for example: (1) the application of dynamic hydrostatic loading of hydrogels with microbubbles. This could provide a physical stimulus (akin to dynamic deformational loading) that would take advantage of the compressibility of air over water; (2) The use of microbubbles to incorporate growth factors into a hydrogel; and (3) Applying different chemical stimulus above and below the floating constructs to take advantage of the fact that microbubble-laden hydrogels float.

The ability to supply nutrients to cells is a useful feature of engineered tissues but an overly porous scaffold can result in cell product loss to the culture medium rather than its retention. An insufficiently porous scaffold or medium can lead to nutrient deficiencies for cells at the construct core region (e.g., regions remote from perfused surfaces). Striking a balance is challenging as construct dimensions increase or as cells deposit matrix with time in culture. A preferred scaffold has a global architecture that uniformly distributes nutrients throughout while maintaining an optimal local pore-structure around cells.

Hydrogels have been adopted for cartilage basic science and tissue engineering due to their high water content, ability to maintain the chondrocyte phenotype as well as ease of uniform cell seeding. An optimized media formulation may be combined with the application of dynamic deformational loading to cell-seeded hydrogel constructs to promote the development of engineered cartilage with native tissue mechanical properties via physical cues to cells as well as enhanced solute transport.

Figure 15:
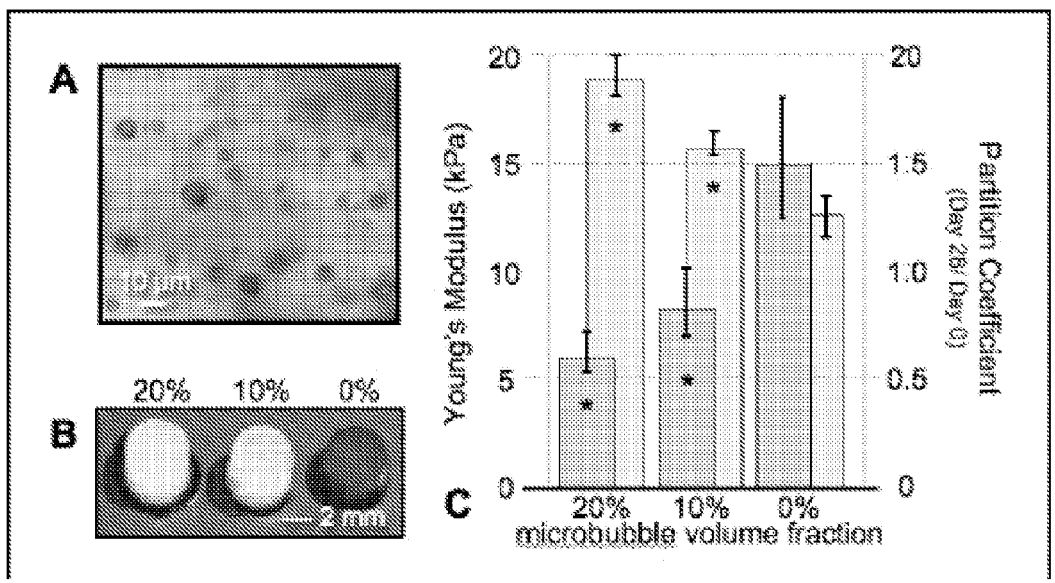
FIGS. 15A-15C show microbubbles in solution, hydrogel with increasing microbubble volume fraction and properties of microbubble infused acellular hydrogels.
Figure 16:
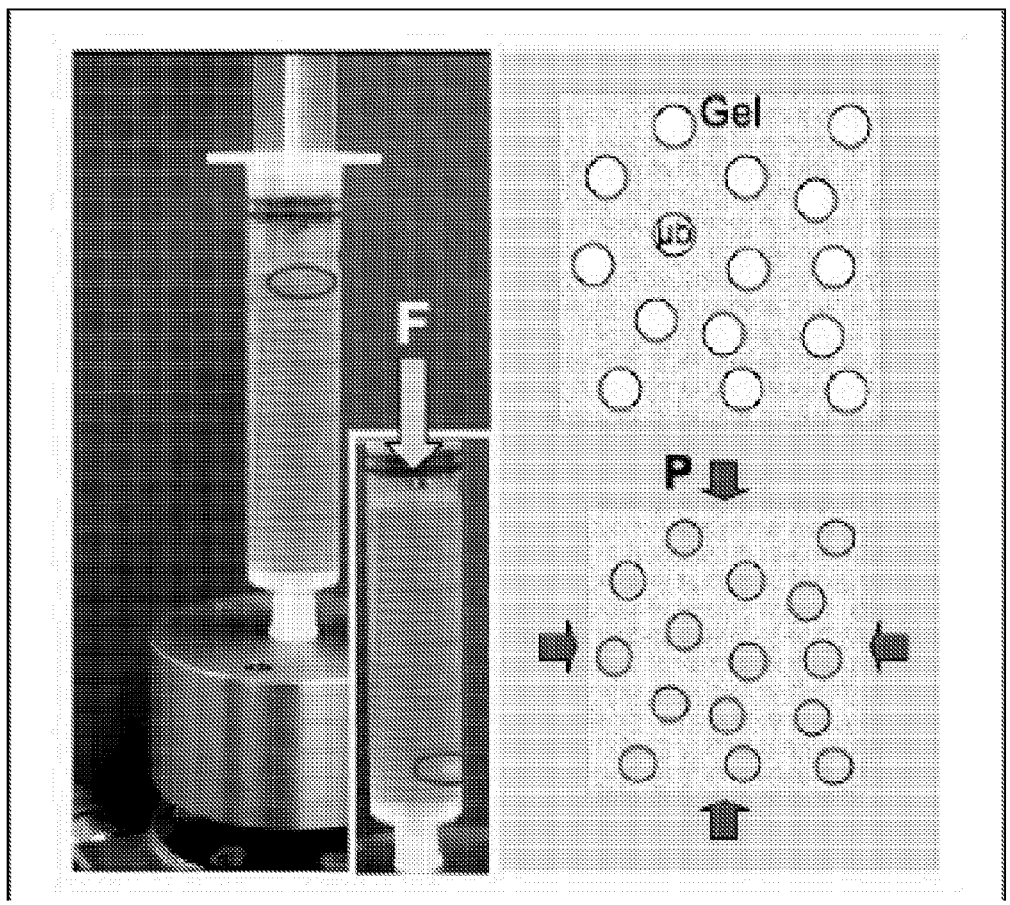
FIG. 16 shows gas-filled microbubble (noted by red ellipse) in hydrogel constructs subjected to hydrostatic pressure and becoming fluid-filled.
Figure 17:
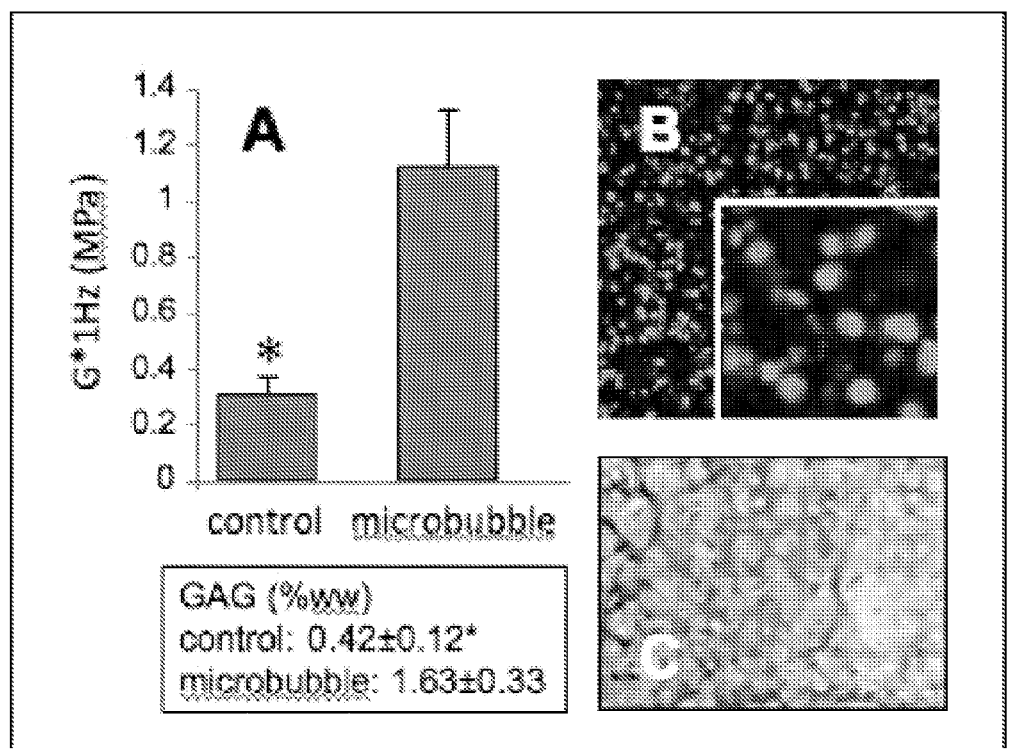
FIGS. 17A-17C show dynamic modulus (G*), vital staining and safranin-O staining for GAG of chondrocyte-seeded agarose constructs infused with microbubbles and cultured for 28 days.

Microbubble technology may provide means for fabricating cell seeded hydrogel scaffold constructs that retain an optimal polymer crosslinking density for extracellular matrix (ECM) production while providing a uniform macro-porosity that increases the effective diffusivity of soluble factors into cell-seeded scaffolds. In the disclosed approach, a suspension of microbubbles and cells are mixed with unpolymerized hydrogel and then permitted to gel (see FIG. 14). When the dissolution of the biocompatible gas is triggered, the microbubbles become fluid-filled, (FIG. 16). At this time, fluid-filled pores act to bridge regions of cell seeded crosslinked hydrogel, decreasing the effective nutrient path length (FIG. 9) and increasing solute diffusivity. This effect has been confirmed as indicated in laboratory data shown in FIGS. 15 and 16. The effect leads to increased tissue properties relative to microbubble-free control gels (FIG. 17). Microbubble infused hydrogel scaffolds may exhibit increasing solute diffusivity in a microbubble dose-dependent manner.

Experiments have established that a tissue construct fabricated from chondrocyte-seeded hydrogel constructs with initial microbubble concentrations yielded 25%, 50%, and 100% greater diffusivity of fluorescently labeled dextran (70 kDa) than the hydrogel without microbubbles. Chondrocyte-seeded, hydrogel scaffolds incorporated with microbubbles may yield engineered tissues with properties closer to the native tissue compared to the same scaffolds without microbubbles. The properties of constructs with microbubbles may be dependent on timing of microbubble dissolution. Application of applied dynamic deformational loading may enhance the beneficial effects of microbubble infused hydrogels. Using predefined microbubble conditions, constructs may be cultured for predefined intervals (e.g., 56 days) and dissolution of gas-filled microbubbles triggered at one or more specific times along the time line. For example, they may be triggered on day 0 or day 14 of a 56 day interval.

Gas filled microbubbles may provide hydrogel scaffold that can be compressed, for example, isotropically. Such a deformation capability may be provided to create a corresponding type of mechanical stimulation to promote cell growth. In embodiments, the susceptibility to be isotropic compression may be modified by selective dissolution of microbubbles.

Cell access to fluid-filled macro-pores may be used to decrease nutrient path length and provide additional space for tissue elaboration at culture points when tissue is denser. Their benefit may be of greatest significance to continued functional tissue development (see FIG. 12).

Figure 10:
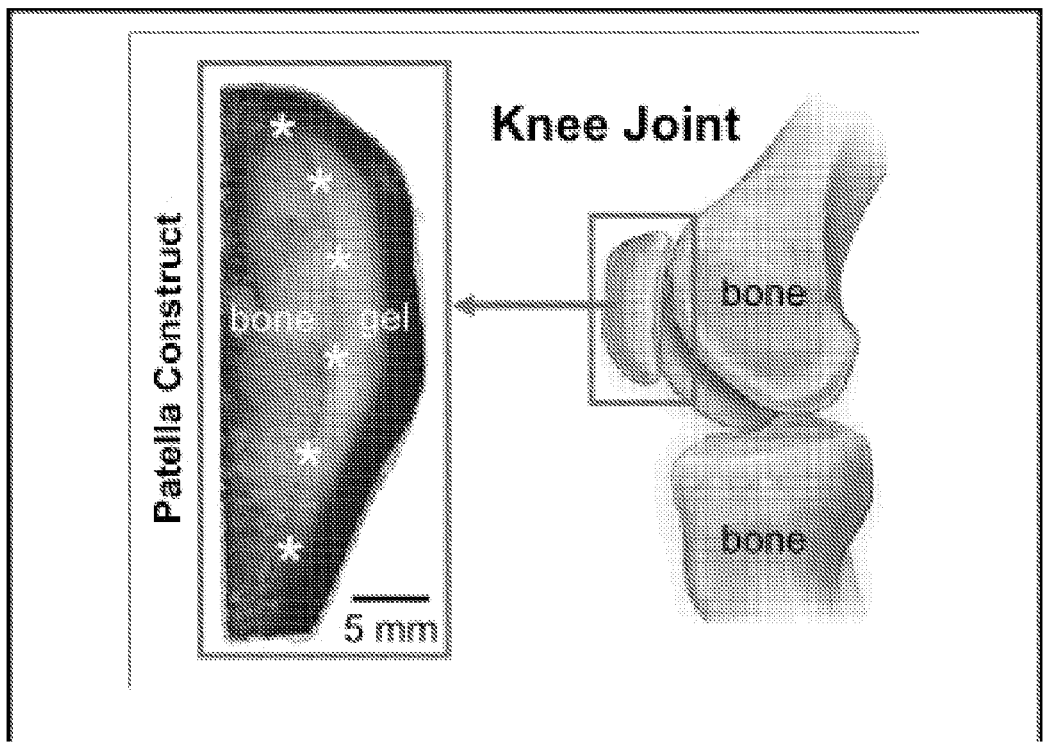
FIG. 10 shows an engineered knee cap (patella) construct with proteoglycan-rich matrix (red safranin-O stain) limited to gel periphery indicating diffusion limitations.

The scaling of engineered tissues aimed at repair of focal cartilage defects to much larger articular constructs indicated for repair/replacement of joints suffering from severe trauma and degenerative joint disease may require the fabrication of tissues with native mechanical properties which are reliant in part on the ability to provide sufficient nutrients to cells residing in the growing tissue, see FIG. 10. The relatively low tissue properties achieved reflect the development of inhomogeneous tissue properties through the engineered construct thickness that develop with culture time. It has been observed that constructs of greater than 1 mm thickness develop a "u-shaped" axial distribution of properties with central regions having less matrix elaboration relative to stiffer peripheral regions.

In embodiments, the composition of a microbubble is a gas core stabilized by a shell comprised of proteins, lipids or polymers. The macro-porosity of bioscaffolds is typically formed using sacrificial porogens that are dissolved away, leaving behind their vacated space. Lyophilization of hydrogels (such as for hyaluronan and collagen) can result in sponge-like scaffolds with macro-porosity. For these systems, cells are introduced via various seeding techniques that depend on the effectiveness of cell infiltration to central regions of the construct to achieve uniform seeding. Unlike hydrogels, pore sizes in these constructs are constrained to a minimum diameter that allows for cell infiltration.

Figure 12:
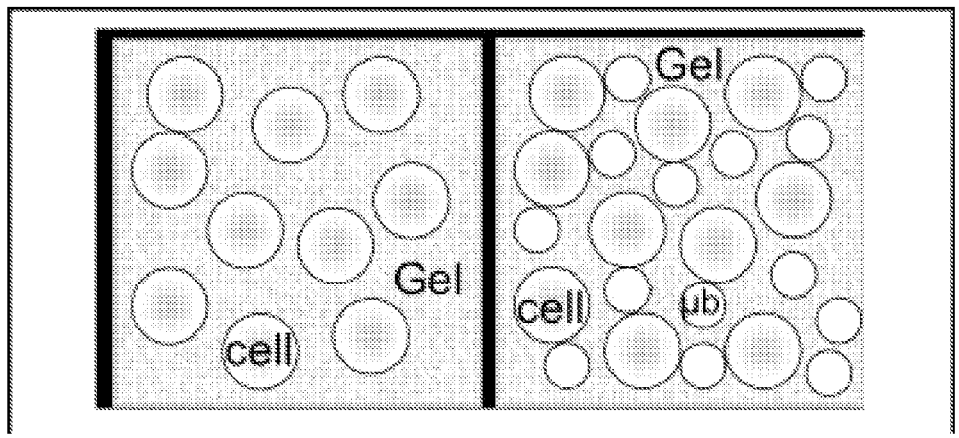
FIG. 12 is a schematic of hydrogel conditions relevant to the disclosed subject matter illustrating cellular constructs with and without microbubbles.

A strategy to introduce macro-porosity to hydrogels in their hydrated form typically adopted for biological applications may include the mixing of unpolymerized hydrogel (liquid) with cells and gas-filled microbubbles followed by activation of hydrogel polymerization, resulting in a suspension of cells and microbubbles in a (solid) cross-linked hydrogel (FIGS. 12, 14). To create macro-porosity, the gas-filled microbubbles may be triggered to dissolve (such as by application of hydrostatic pressurization, Section P2—FIG. 16), releasing their biocompatible gas, and vacating a pore space that is immediately filled with culture media.

Figure 9:
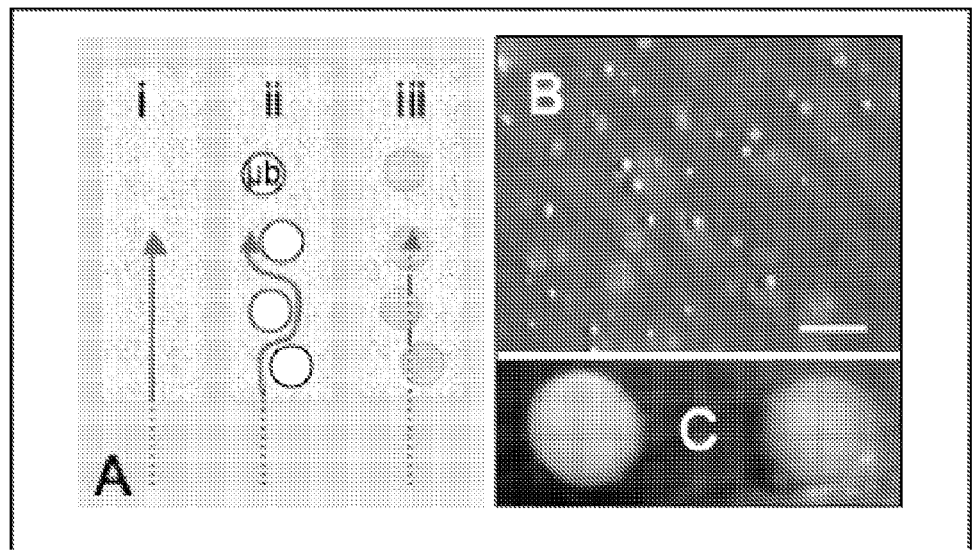
FIG. 9A shows a schematic of solute diffusion paths in (i) hydrogel; (ii) hydrogel with gas microbubbles (μb); and (iii) fluid-filled pores after μb dissolution.
FIG. 9B shows microbubbles suspended in hydrogel.
FIG. 9C shows microbubble infused hydrogel construct pre/post partial microbubble dissolution was triggered (becoming less opaque).

As microbubble dissolution can be controlled, cell access to fluid-filled macro-pores can be timed so as to decrease nutrient path length and provide additional space for tissue elaboration at later culture points when tissue is denser and their benefit may be of greatest significance to continued functional tissue development (see FIGS. 9 and 13).

Figure 11:
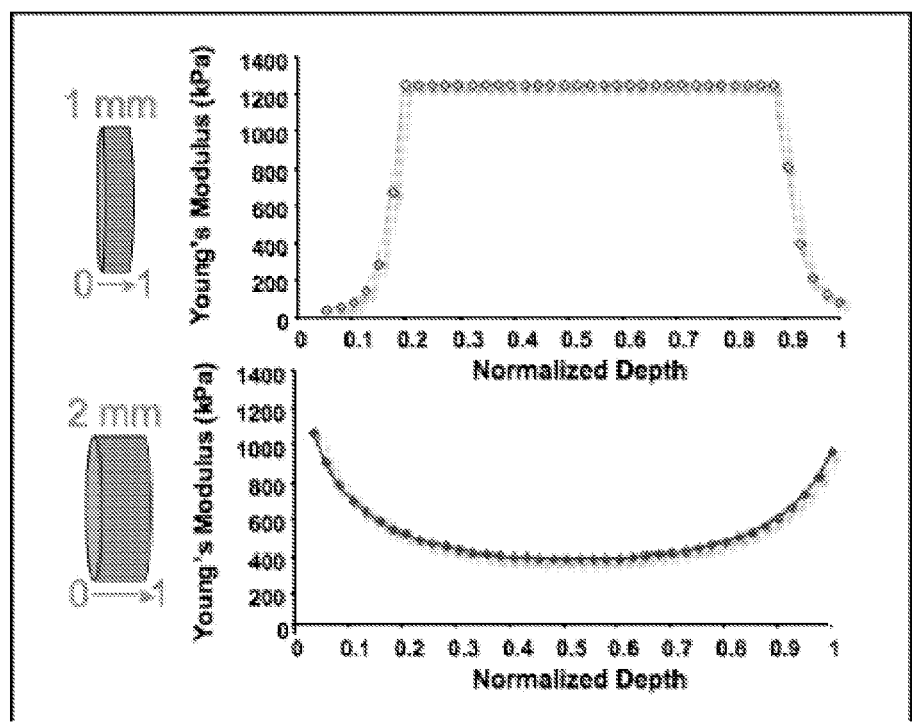
FIGS. 11A and 11B show differences in properties for varying construct thicknesses.
Figure 13:
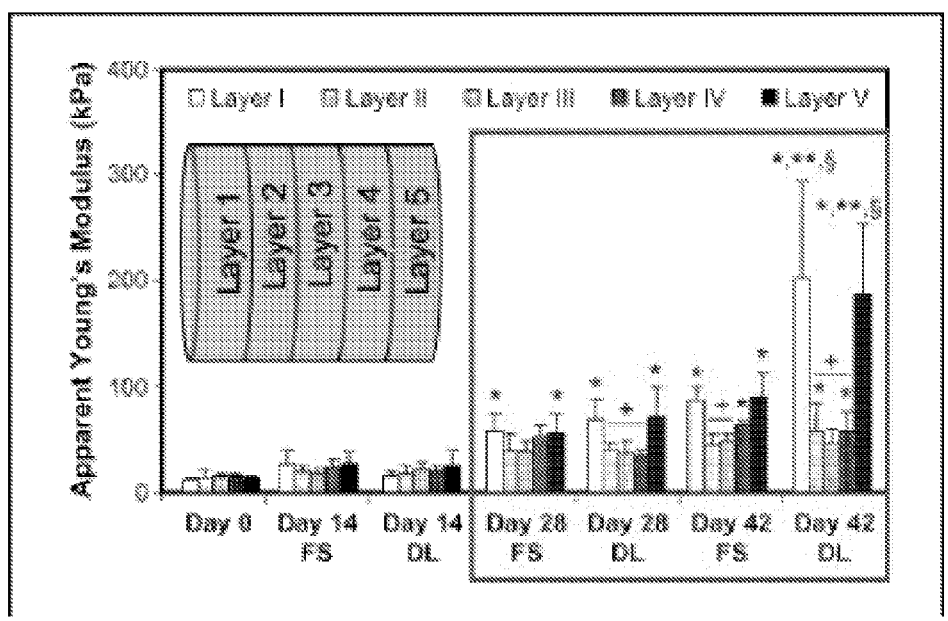
FIG. 13 is a graph illustrating chondrocyte-seeded agarose hydrogel construct mechanical properties varying with culture time.

Adopting a functional tissue engineering approach, optimized media conditions have been demonstrated (FIG. 11) and applied dynamic deformational loading has been shown to promote mechanically functional engineered cartilage development of juvenile and adult chondrocytes, FIG. 13. Solute uptake by agarose hydrogel constructs and cartilage can be increased by a factor on the order of ten-fold with applied deformational loading compared to free-swelling controls. This effect is more pronounced for large solutes, as small solutes can diffuse more readily.

For purposes of this initial characterization, we studied a non-degradable hydrogel with microbubbles that ensures that changes to tissue properties can be attributed to cell activities only. Embodiments employ agarose hydrogel, a scaffold that has supported in vitro functional engineered cartilage development, shown good biocompatibility in canine preclinical model and tested in phase III clinical trials in Europe as a copolymer in a $3^{rd}$ generation autologous chondrocyte implantation. Embodiments may employ other candidate hydrogels, where the general benefits associated with hydrogel scaffolds including relative ease of uniform cell seeding, hydrophilic nature, ability to modulate polymer cross-linking density, as well as form various shapes and sizes is preserved.

Microbubble Methods

Microbubble strategies are summarized in Table 1. Cell Source: Articular chondrocytes will be enzymatically harvested from bovine carpo-metacarpal joints from freshly slaughtered 4-6 month old calves obtained from a local abattoir. Juvenile bovine chondrocytes are a well-established model for cartilage research and have demonstrated robust tissue growth and mechanically functional tissue development in our cartilage tissue engineering studies. After construct fabrication (described below), constructs will be maintained in culture for up to 56 days, with three-times weekly changes of chondrogenic growth medium (with 5 g/mL proline, 1% ITS+, 100 nM dexamethasone, 50 pg/mL ascorbate, and 10 ng/mL of TGF-3 for the first 2 weeks). During culture time, medium samples will be collected to analyze glycosaminoglycan (GAG) release in order to determine the relationship between GAG synthesis and retention in hydrogels with various microbubble concentrations. Collagen will also be monitored, but we anticipate negligible media levels of collagen since our enzymatic digestion studies indicate that collagen forms an interconnected network.

Construct Fabrication

Microbubbles can be created through sonication of distearoyl phosphatidylcholine (DSPC) lipid in perfluorobutane (PFB) gas. The resulting bubble mixture will be counted and sized (~0.5-10 um) using a technique to determine total gas volume. Gas volume fraction can be verified with construct buoyancy measurements. One volume of low-melt agarose (Type VII, Sigma) at 4% grams agarose/ml PBS will be mixed with an equal volume of cell suspension ($60 \times 10^6$ cells/ml of microbubble solution in media) at 37 C and gelled in sterile molds to yield a final cell concentration of $30 \times 10^6$ cells/ml in 2% w/v agarose with the desired concentration of microbubbles. Disks of 4 mm diameter will be cored out using a biopsy punch. Two-percent weight/volume agarose (Sigma, Type VII) has been shown to be more optimal than 1% and 3% w/v gels, with the 1% gels not retaining enough cell synthesized products and 3% gels providing too dense an environment to supply nutrients to central portions of the construct). As with most hydrogels, the increased gel concentration results in smaller tissue pores (and lower solute diffusivity).

Triggered Gas Dissolution

Microbubbles embedded in the agarose scaffold will be purged of gas through the application of hydrostatic pressure (~289 kPa) by compressing a sterile, capped syringe in an Instron testing rig (as shown in Section P2). The efficiency of gas removal will be quantified by the difference in wet weight before and after the application of hydrostatic pressure or by construct buoyancy measurements. Most of the gas can be expelled in this manner. Control disks will be subjected to the same experimental set up to account for any effects of the transient applied pressure, which is more than an order of magnitude lower than physiologic pressures during joint loading. An alternative strategy of gas removal is via vacuum degassing of the media.

Assessment of Construct Properties

Whole-construct mechanical properties (E and G*) will also be assessed via a custom testing device while construct-level diffusivity will be assessed by maintaining constructs in a bath of fluorescently labeled of 70 kDa dextran and reporting the uptake ratio (RU) of dextran captured inside the disk to that of the bathing solution, as previously described. Dextran is a hydrophilic polysaccharide available in a range of molecular weights (3 to 2000 kDa), and has low toxicity, is relatively inert and has good water solubility. Whole construct mechanical properties, the compressive Young's modulus and dynamic modulus (G*, a functional measure that reflects construct radial tensile properties and hydraulic permeability), will be determined as previously described. Local mechanical properties will be assessed via digital image correlation on a custom microscope testing device while local diffusivity will be assessed via fluorescence recovery after photobleaching (FRAP) measurements as previously described. Biochemical assessment of constructs will include GAG (DMMB assay), collagen (OHP assay), and ELISAs for type I and II collagen expressed as percentage wet weight (or DNA content via the Picogreen assay) will be quantified as routinely performed in the laboratory, along with histology (safranin-O, picosirius red, immunohistochemistry for collagen types, and polarized light for fiber organization).

Statistical Analyses

For a large effect size of 0.4, and significance at $p<0.05$, n=5 disks per time point yields a power greater than 0.91. We have designed our studies to yield n=6 samples for each test in case of sample loss. Post-hoc analyses was done using ANOVA with Tukey's post hoc test using Statistica (StatSoft, OK). Additionally, the strength of relationship between matrix characteristics (mechanical strength and diffusivity)

and tissue growth will be analyzed using Pearson's correlation test. Each study was repeated at least twice using cells from independent cell preparations. Cells for an experiment are typically combined from wrist joints of 3-4 animals.

In embodiments, 10% peak-to-peak deformation is applied to scaffolds at 1 Hz without lift-off effects (i.e., separation of the loading platen from the sample). The microbubble stability may be increased via saturating the culture media with PFB gas to minimize gradients leading to gas efflux. Additionally, microbubble dissolution can be triggered at later points in culture.

Acellular microbubbles (polydisperse 0.5-10 μm) may be fabricated from vigorous shaking of distearoyl-phosphatidyl-choline (DSPC) lipid in the presence of perfluorobutane (PFB) gas using a dental amalgamator. The resulting bubble mixture was suspended in PBS solution (A) or molten agarose (Type VII, Sigma) where cylindrical discs ((/)4×2.3 mm) were cast (A, inset; B), microbubble dissolution triggered (Section P2 below) and cultured for 28 days. Increasing microbubble concentration (0, 10, 20% v/v fraction) increased the turbidity of the constructs, making them appear more opaque (B) and decreased the construct modulus (C). The partition coefficient (defined as the ratio of construct/bath solute concentration determined using fluorescently-labeled 70 kDa dextran as described above) increases with microbubble concentration, indicating that microbubbles enhanced solute transport into the constructs, FIG. 15.

Acellular microbubble constructs prepared in Section P1 above (20% v/v) were suspended in PBS in a 30 CC syringe (Becton Dickenson) with a luer plug at the syringe outlet, yielding a sealed fluid-filled chamber with a small volume of air below the syringe piston. The syringe was positioned axially on a table-top Instron device with the piston against the loading ram and a force (F) of 100 N applied (289 KPa). The construct was initially floating (near the piston) and as pressure was applied, the construct sank to the bottom as gas release from the microbubbles was triggered and their remnant pores became fluid-filled. Construct sinking is attributed to increased density associated with compression of the gas-filled microbubbles, thereby reducing its buoyancy. This buoyancy force is restored as the microbubbles become uncompressed. These observations demonstrate the feasibility of applying hydrostatic pressurization to microbubble incorporated hydro gel constructs in order to affect microbubble dissolution, FIG. 16.

Microbubbles were fabricated as in Section P1 but with primary chondrocytes (60×10 cells/mL) isolated from fresh bovine wrist joints and suspended in equal volume molten agarose (Type VII, Sigma), see FIG. 14. Cylindrical discs ((/)4×2.3 mm, 30×$10^6$ cells/mL) were cast, bubble dissolution triggered via hydrostatic pressure (Section P2 above) and cultured for 28 days in chemically-defined medium according to an optimized protocol. After 28 days in culture, constructs exhibited viable cells, and increased dynamic modulus and GAG content relative to microbubble-free control constructs. This study demonstrates the biocompatibility of microbubble infused hydro gel scaffolds and their ability to enhance cartilaginous tissue formation relative to control gels, FIG. 17.

It will be appreciated that the controller described above can be implemented in hardware, software, or both. For example, a dynamic loading controller can be implemented, for example, using a processor configured to execute a sequence of programmed instructions. The processor can be for example, but not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as C++. The instructions can also comprise code and data objects provided in accordance with, for example, the Visual Basic™ language, or another object-oriented programming language. The sequence of programmed instructions and data associated therewith can be stored in a non-transitory computer-readable medium such as a computer memory or storage device which may be any suitable memory apparatus, such as, but not limited to ROM, PROM, EEPROM, RAM, flash memory, disk drive and the like. A computer program product can include the instructions and a computer-readable medium as described above.

Furthermore, the controller can be implemented as a single processor or as a distributed processor. Further, it should be appreciated that the steps mentioned above may be performed on a single or distributed processor. Also, the processes, modules, and sub-modules described in the various figures of and for embodiments above may be distributed across multiple computers or systems or may be co-located in a single processor or system. Exemplary structural embodiment alternatives suitable for implementing the controller described herein are provided below.

The controller described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a PLD, PLA, FPGA, PAL, or the like. In general, any process capable of implementing the functions or steps described herein can be used to implement embodiments of the method, system, or a computer program product (software program).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a VLSI design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of the mechanical, tissue engineering and/or computer programming arts.

Moreover, embodiments of the disclosed method, system, and computer program product can be implemented in software executed on a programmed general purpose computer, a special purpose computer, a microprocessor, or the like.

It is, therefore, apparent that there is provided, in accordance with the various embodiments disclosed herein, a microbubble devices, methods and systems.

While the invention has been described in conjunction with a number of embodiments, it is evident that many alternatives, modifications and variations would be or are apparent to those of ordinary skill in the applicable arts. Accordingly, Applicants intend to embrace all such alternatives, modifications, equivalents and variations that are within the spirit and scope of the appended claims.

TABLE 1

Summary of strategies for construct fabrication and assessment.

| | Scaffold Fabrication Strategy |
|---|---|
| Cell type | Juvenile bovine chondrocytes |
| Cell Concentration | $30 \times 10^6$ cells/mL in hydrogel |
| Hydrogel | Agarose (2% weight/volume, Type VII, Sigma) |
| Microbubble shell | DSPC Lipid [16, 37] |
| Microbubble Gas | Perfluorobutane (PFB) Gas |
| Triggered Gas Dissolution | Hydrostatic Pressure (Preliminary Data P2) |
| Microbubble Size/Conc. | Polydisperse via Accusizer |
| Microbubble Dissolution | Wet weight change after triggered dissolution |
| Construct Material *Propertie* | Equilibrium (EY) and Dynamic modulus (G *) Dextran partition coefficient [2, 12] |
| Local Material Properties | Local E Y, G * via digital image correlation microscope testing Local diffusivity via FRAP |
| Biochemical Properties | DNA/wet weight, GAG/wet weight Collagen/wet weight (ELISA for type I -II) Histology/Immunohistochemistry/ polarized light [8, 19, 29] |

What is claimed is:

1. A method of mechanically stimulating cells in a hydrogel, the method comprising:
   incorporating gas-filled microbubbles into the hydrogel;
   seeding the hydrogel with cells; and
   compressing the hydrogel with the gas-filled microbubbles incorporated therein so as to produce a non-zero divergence of a volume in a portion of the hydrogel during a culturing cycle.

2. The method of claim 1, wherein, during the culturing cycle and before the compressing, the microbubbles are gas-filled.

3. The method of claim 1, wherein the microbubbles have a shell comprising a protein, lipid or polymer.

4. The method of claim 1, wherein the seeding includes seeding the hydrogel with chondrocyte cells.

5. The method of claim 1, wherein the microbubbles are incorporated into the hydrogel before the hydrogel is polymerized.

6. The method of claim 1, wherein the compressing occurs at a predetermined time during the culturing cycle.

7. The method of claim 1, wherein a programmed controller transmits a signal to an actuator to perform the compressing.

8. The method of claim 1, further comprising, prior to the compressing, culturing the cells in the hydrogel with gas-filled microbubbles incorporated therein.

9. The method of claim 8, wherein said compressing is such that at least some of the microbubbles in the hydrogel dissolve so as to release gas from within and allow cell culture medium to fill spaces vacated by said gas, and further comprising, after the compressing, further culturing the cells in the hydrogel.

10. The method of claim 1, wherein each microbubble has a shell comprised of distearoyl-phosphatidylcholine (DSPC) and is filled with perfluorobutane (PFB) gas.

11. The method of claim 1, wherein each microbubble has a size in the range of 0.5 μm to 10 μm.

12. The method of claim 1, wherein the microbubbles are incorporated into the hydrogel at a concentration of $1 \times 10^8$ to $1 \times 10^9$ microbubbles/mL.

13. The method of claim 1, wherein said compressing comprises hydrostatic loading of the hydrogel.

14. A method comprising:
   incorporating gas-filled microbubbles into a hydrogel;
   seeding the hydrogel with cells; and
   isotropically compressing the hydrogel with the gas-filled microbubbles incorporated therein by applying a hydrostatic loading during a culturing cycle of the cells seeded in the hydrogel so as to produce a non-zero divergence of a volume in a portion of the hydrogel.

* * * * *